United States Patent [19]

Astle

[11] 4,287,301
[45] Sep. 1, 1981

[54] METHOD AND APPARATUS FOR STREAKING AGAR

[76] Inventor: Thomas W. Astle, 607 Harbor View Rd., Orange, Conn. 06477

[21] Appl. No.: 679,016

[22] Filed: Apr. 21, 1976

[51] Int. Cl.³ .................. C12Q 1/24; C12M 1/26; C12M 1/32

[52] U.S. Cl. .................. 435/30; 435/292; 435/293

[58] Field of Search ............ 195/103.5 R, 127, 139; 73/425.6; 435/30, 292, 293

[56] References Cited

U.S. PATENT DOCUMENTS

| | | | |
|---|---|---|---|
| 3,501,379 | 3/1970 | Tate | 195/127 |
| 3,681,030 | 8/1972 | Natelson | 73/425.6 X |
| 3,778,351 | 12/1973 | Roson | 195/127 |
| 3,799,844 | 3/1974 | Campbell et al. | 195/127 |
| 3,844,896 | 10/1974 | Sharpe | 195/103.5 R |
| 3,850,754 | 11/1974 | Wilkins et al. | 195/127 |

OTHER PUBLICATIONS

BBL Manual of Products and Laboratory Procedures, pp. 1, 2, & 3, Fifth Edition, 1968, BBL Division of Becton, Dickinson and Company.

*Primary Examiner*—Robert J. Warden
*Attorney, Agent, or Firm*—DeLio and Montgomery

[57] ABSTRACT

A method and apparatus for streaking a sample on agar plates where the sample is dispensed from a flexible tube which is oscillated while the plate is rotated. The plates are stored in a refrigerated compartment and selectively presented to a transfer position where they are transferred to a first position to have a lid removed, to a second position to be streaked, and third position to be re-lidded and moved to a classification stack for removal to an incubator.

40 Claims, 11 Drawing Figures

METHOD AND APPARATUS FOR STREAKING AGAR

This invention relates to microbiology and more particularly relates to apparatus and method to streak a specimen over agar surfaces to provide identification of the specimen.

Streaking of specimens on an incubating media generally known as agar to determine cultures of a microorganism is widely known. For many years such streaking of the specimen in differing concentration has been accomplished.

In practice, from two to four plates of various types of agar are used for each specimen. The type of agar used is a function of where the specimen originated and the anticipated microorganisms. The agar may be streaked with the specimen very quickly manually by a skilled technician. However, a considerable number of man hours are expended in streaking a number of agar specimens, including various aspects of the operation. The agar plates or dishes must be obtained from refrigeration storage, sorted to the various types of agar, then selected for each specimen, marked with that specimen number, streaked either for isolation or for colony count, collected and then restacked for the appropriate incubator.

There have been a number of devices suggested to decrease the time requirement in streaking an agar plate, or improve the streaking quality. However, such devices have not proven entirely satisfactory in that special plates may be required, or that such devices usually take as long or longer to use than a skilled technician manually streaking the plate. Therefore, improved streaking accuracy that may be provided does not alone justify the expense of the device.

The present invention provides a new and improved streaking apparatus and method in which the agar plates with lid on are stored under refrigeration in classified columns of a rotatable magazine. The magazine may be positioned to present any column of agar plates to a transfer mechanism. Such transfer mechanism transfers a plate to a first position where the lid is removed. Then the plate is transferred to a streaking position where it is automatically streaked with a selected specimen. The plate is then transferred to a lid-on position and lifted up to its lid. Thereafter, a transfer mechanism slides the innoculated plate to a classification zone where it is lifted into a selected stack of plates.

The invention further provides a new and improved streaking device and method where the specimen is aspirated into a flexible tube by a roller-pump, and the tube is moved over a plate and brought into contact with the agar in an arc with the open end of the tube trailing. The tube is oscillated while the plate is rotated and translated while the roller pump ejects the specimen. The apparatus provides means for drawing tubing from a supply reel, and cutting off a used length so that on each streaking operation, a fresh supply of tubing may be utilized.

An object of this invention is to provide a new and improved apparatus for streaking a liquid specimen on agar.

Another object of this invention is to provide a new and improved method of streaking agar.

A further object of this invention is to provide a new and improved method and apparatus for storing, transferring, streaking and classifying plates containing agar.

A still further object of this invention is to provide a new and improved apparatus for handling and streaking agar samples including lid removal, transfer and lid replacement.

The features of the invention which are believed to be novel are particularly pointed out and distinctly claimed in the concluding portion of this specification. However, the invention both as to its organization and methods of operation, together with further objects and advantages thereof may best be appreciated by reference to the following detailed description taken in conjunction with the drawing, wherein:

To facilitate the understanding of the invention the basic steps of the process are first described. A multiplicity of columns each containing a plurality of prepared agar in plates such as Petrii dishes with lids thereon are stored in classified columns in a magazine-like mechanism, according to agar type. The plates in each column are spring-biased upwardly so that as that column is moved to a predetermined position the uppermost dish is in a position to be transferred for a streaking operation. When the dish is in such a position a transfer slide moves the dish to a position where the lid is removed. Then the plate is transferred to a position in which it is streaked with a specimen. Thereafter, the plate is transferred to a position where it is moved upwardly into contact with its previously removed lid, and the entire plate is moved to a classification and storage position. Such operations occur sequentially on predetermined cycles as will hereinafter be explained.

In the streaking position the plate is both rotated and translated while a streaking mechanism is oscillated back and forth. This permits a predetermined specimen to be uniformly distributed in annular arrays of varying intensity over the surface of the agar.

A mechanism 10 by which the invention may be practiced comprises a frame or housing member 11 defining a refrigerated compartment 12 having a rotatable magazine 13 of agar plates. The magazine comprises a plurality of columns or stacks 14 of agar plates. Each column is defined by a plurality, preferably four, of vertical rods 15. The plates of each column are urged upwardly by a spring 16. Retaining rings 17 overlie the top of the columns 14 but have as an opening therein at one location for removal of agar plates from a selected column to a transfer mechanism as hereinafter described.

Figure 1:
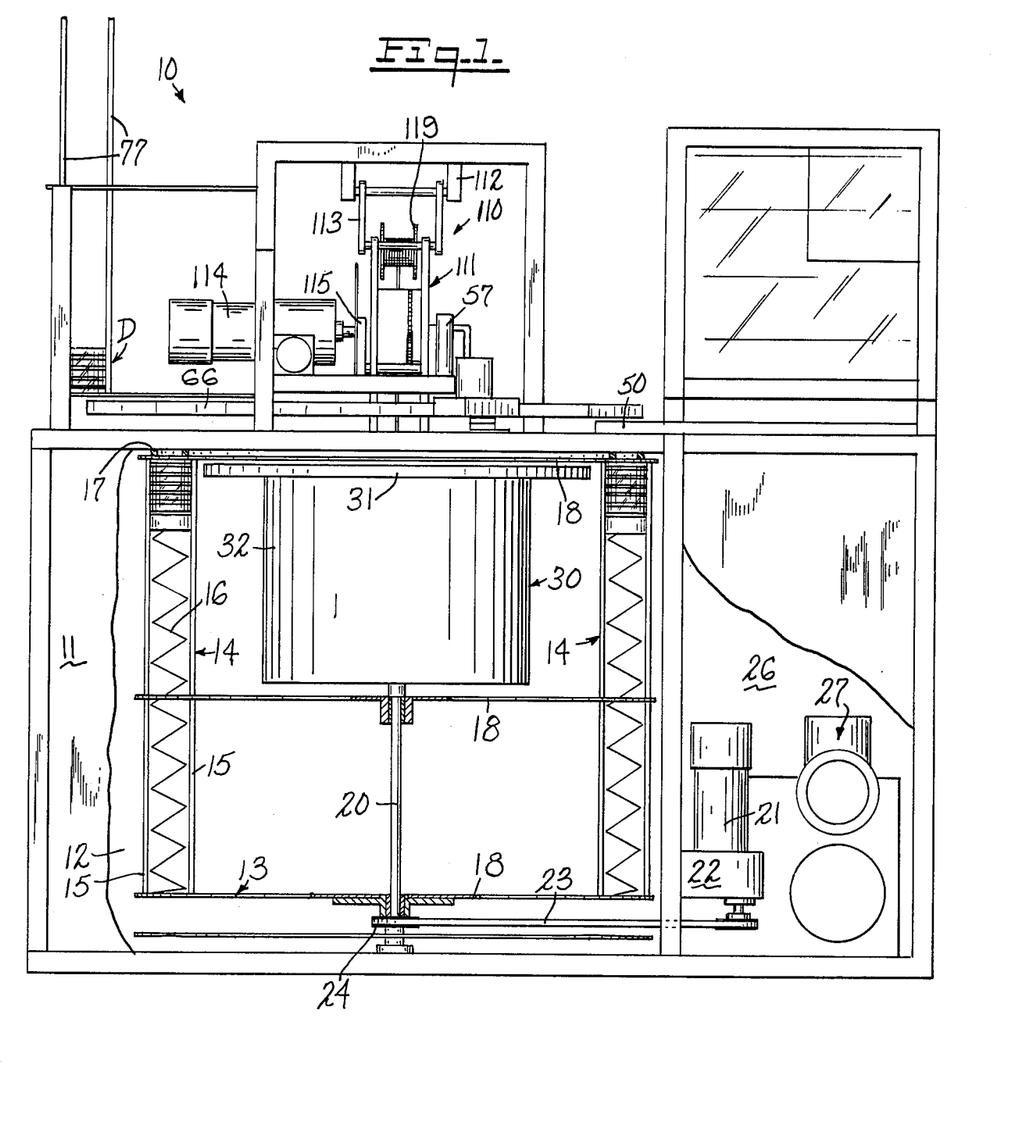
FIG. 1 is a front elevation of apparatus embodying the invention with portions of the cover removed.
Figure 2:
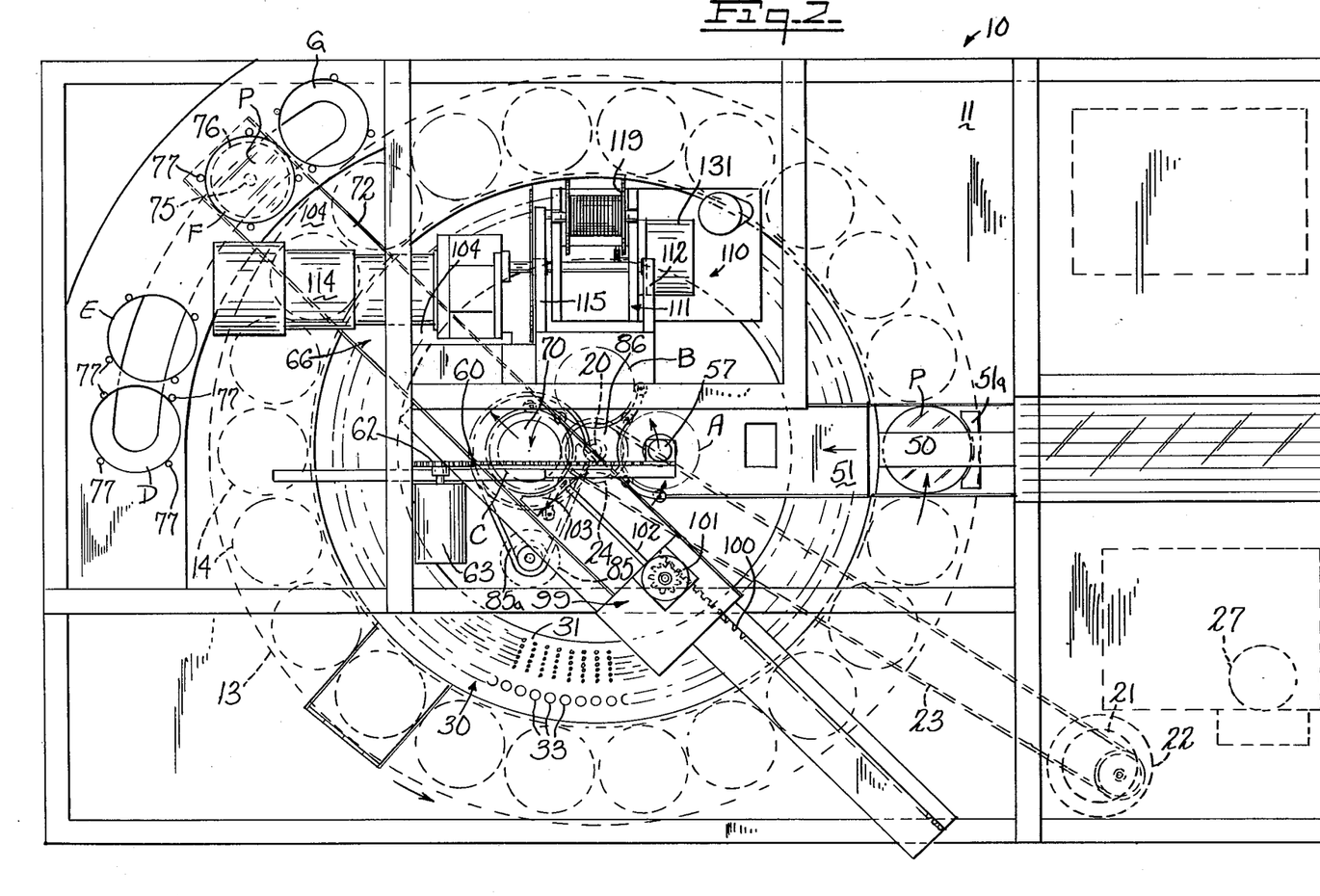
FIG. 2 is a top plan view of the apparatus of FIG. 1.

Columns 14 in an annular array are shown in FIG. 2. The rods 15 are carried in spaced apart support members 18 which are journaled on a shaft 20. A motor 21 and transmission 22 drives magazine 13 through a belt 23 and pulley 24 or chain-sprocket. Compartment 26 also contains refrigeration equipment, generally indicated at 27 to maintain compartment 12, and the agar plates therein at a predetermined temperature.

The motor 21 provides a means for rotating magazine 13 to a predetermined position to off-load agar plates from a preselected one of columns 14.

Figure 3:
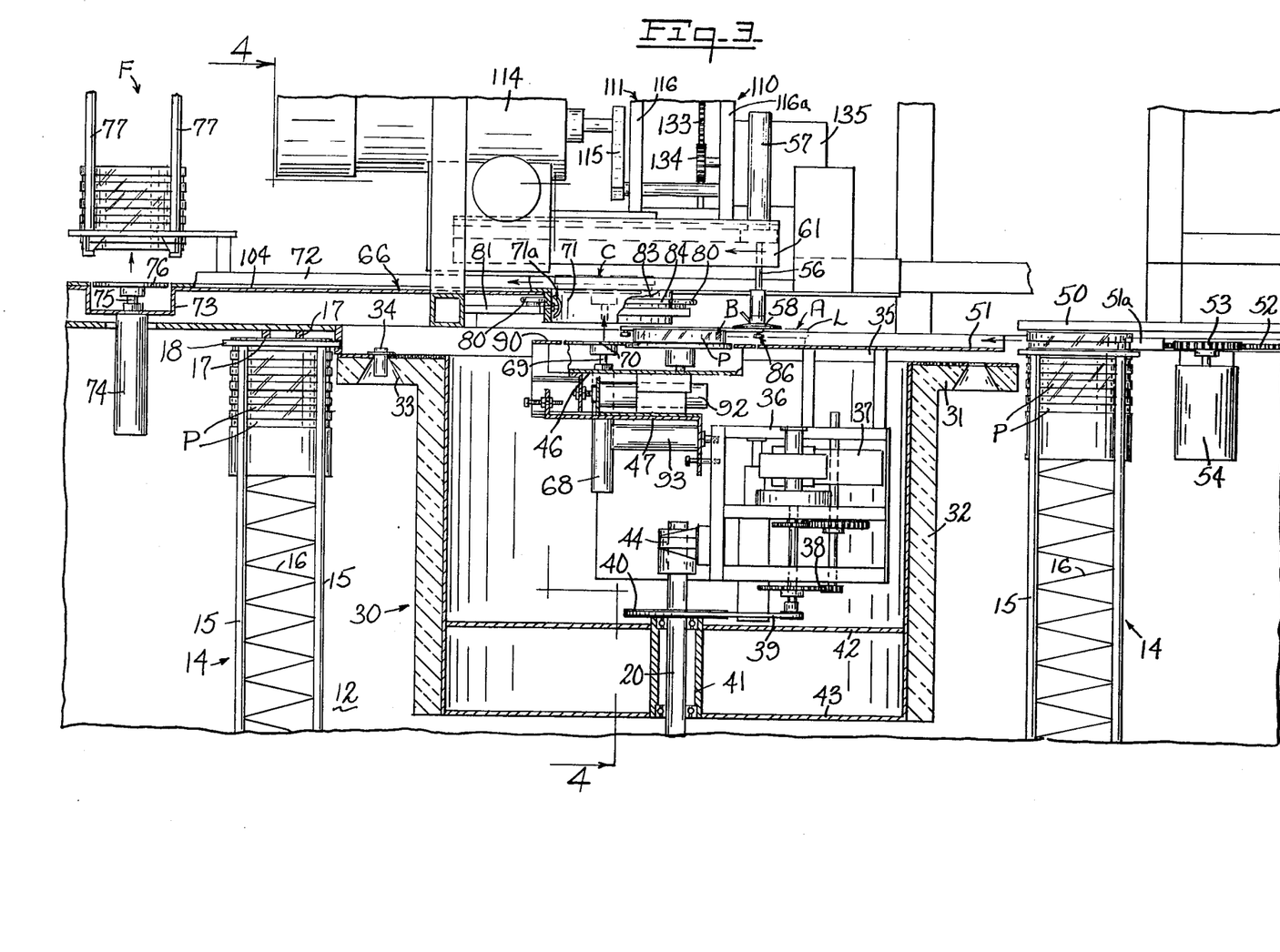
FIG. 3 is an enlarged view of portions of FIG. 1.

A second member 30, having an upper specimen holding ring or table 31 and a depending insulated side wall 32, is rotatable about shaft 20. As shown in FIGS. 2 and 3, table 31 has a plurality of apertures 33 adapted to hold specimen containers 34 therein in an annular array.

Depending from an upper stationary member 35 is a motor 37 and a support structure 36 which supports drive mechanism 38, which rotatably drives member 30 on shaft 20 through a belt 39 and pulley 40 or chain-sprocket. Pulley 40 is fixed to a sleeve shaft 41 carried on stiffening members 42 and 43. A bracket 44 on structure 36 supports a bearing for shaft 20. Motor 37 and drive 38 together with the coupling mechanism provide a means for rotating member 30 and table ring 31. The sidewalls 32 are insulated with in the refrigerated compartment.

Movable platform members 46 and 47 are also supported from structure 36, as hereafter described.

As shown in FIGS. 2 and 3 an agar plate P with lid on is urged upwardly to a transfer position beneath a stop plate 50 in a position to be moved along surface 51 of member 35, to a lid-off position A. Plate P is transferred by a pusher 51 on a rack 52 driven by a pinion 53 on motor 54.

Figure 9:
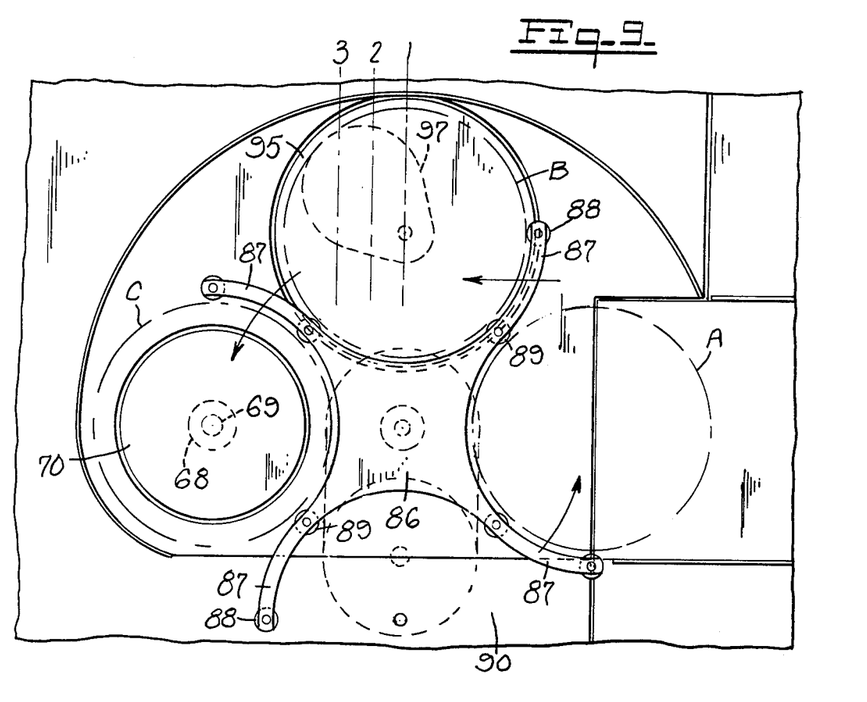
FIG. 9 is a top plane view of a transfer mechanism for agar plates.

As more clearly shown in FIGS. 2 and 9, a plate is received at three stations A, B, and C. At station A the lid is removed, at station B the agar is streaked, at station C, the plate is replaced to the lid, and then transferred to an off-loading position. The transfer of plates to stations B and C is accomplished by the mechanism of FIG. 9, hereinafter described.

At station A, the piston 56 of cylinder 57 (FIG. 3) descends and engages lid L of plate P through a cup 58. Suction is applied to cup 58 and piston 56 is retracted to remove the lid.

Figure 4:
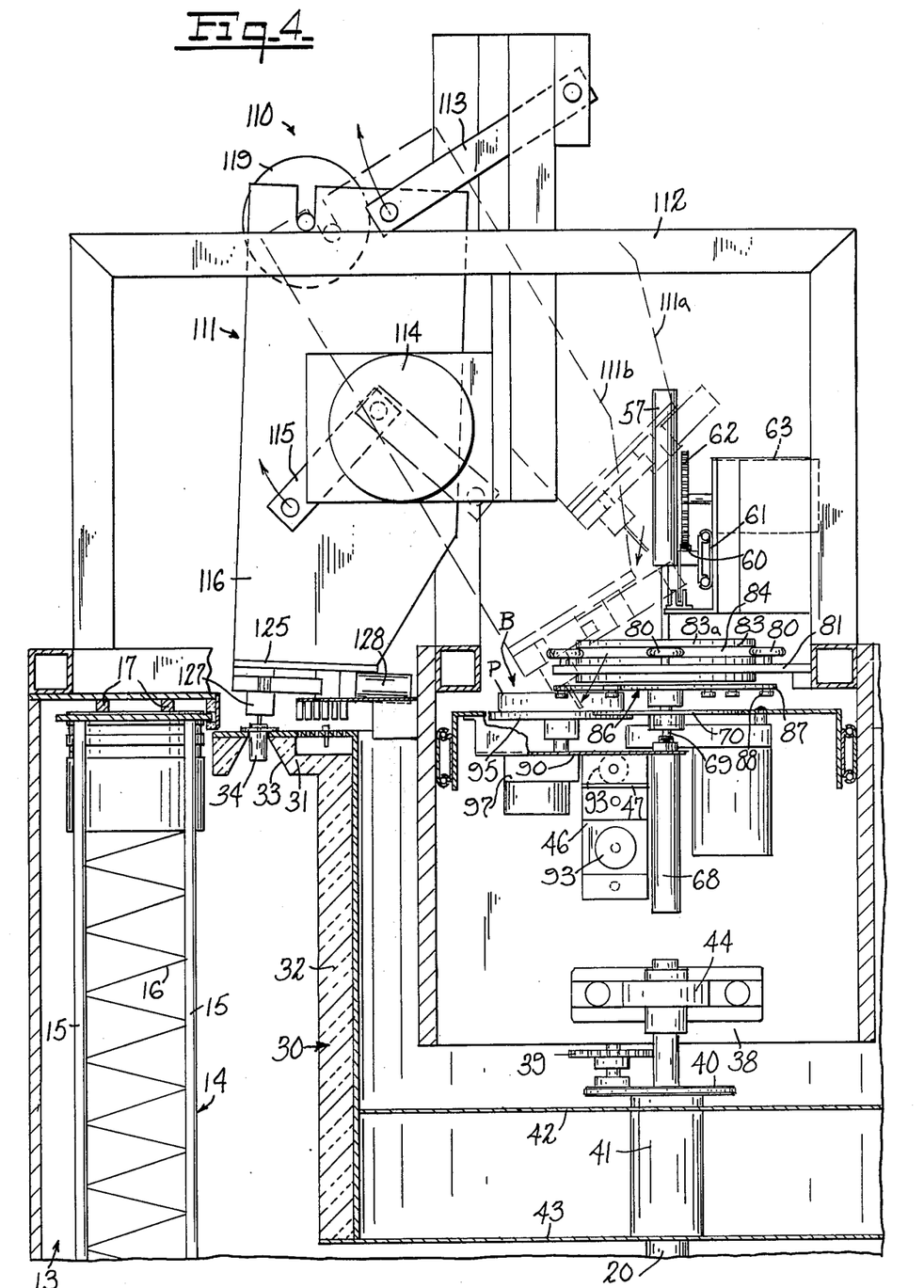
FIG. 4 is a view seen in the plane of lines 4—4 of FIG. 3.

Cylinder 57 is mounted to a rack 60 carried on a guide 61 (FIG. 4). Rack 60 is driven by a gear 62 operated by a drive 63 between a lid-off (A) and a lid-on position (C) as hereinafter described.

A transfer member 66 (FIG. 3) is arranged to provide a guide for a plate to out put classification stacks from a lid-on position. After an agar plate is streaked it is moved to lid-on position C where a cylinder 68 through its piston 69 and a carrier plate 70 thereon lifts the plate through an opening 71 in member 66 to position C shown in broken line in FIG. 3, so that it may be moved along a guideway 72 on member 66 to a classification stack position. Spring clips 71a in opening 71 support a lid thereupon released by cylinder 57. Member 66 includes a support 73 at the end thereof for a cylinder 74 having a piston 75 and lift plate 76 thereon.

As a plate is moved along guideway 72 and placed on lift plate 76, cylinder 74 lifts it into one of stacks D, E, F, or G (FIG. 2). Each of stacks D. E. F and G is defined by four rods 77–80, as shown in FIG. 2. At the bottom of each of the stacks D, E, F and G are one-way pivotal latches (not shown) which permit a plate to be inserted at the bottom of a stack, but provide support and prevent downward removal of a plate.

Member 66 is supported by means of a plurality of bearings 80 carried on a support 81 on the upper portion of frame 11 (FIGS. 3 and 4). Opening 71 is defined in a generally cylindrical member 83 attached to member 66, and has a groove 84 therein which receives support bearings 80. Member 66 is pivoted to the stacks D, E, F, or G by means of a motor 85 (FIG. 2) which drives a chain 85a fitted about portion 83a of member 83.

A transfer member 86 having four arcuate arms 87 with depending rollers 88 and 89 thereon (FIGS. 4 and 9) is rotatably mounted to a translatable plate 90. Plate 90 is carried on platform member 46. Transfer member 86 transfers plates received at position A, successively to positions B and C. Plate 90 is linearly movable in two steps by cylinders 92 and 93 (FIG. 3). Cylinder 92 moves platform member 46 a first linear increment, and thereafter cylinder 93 moves platform 47 another incremental amount or vice versa. A rotatable table 95, driven through a motor-gear drive 47 has an upper surface coplanar with position A. Table 95 is position B. A plate retaining flange 99 on plate 90 retains the plates in arms 87 during indexing.

Thus a plate on table 95 may be rotated, and linearly translated, and then returned. During translation table 95 and lift plate 70 move together.

A plate transfer device on member 66 comprises a member 99 having a rack 100 (FIG. 2) defined thereupon which is engaged by a pinion of motor 101 (FIG. 2). A rod 102 extends from member 99 and has an arcuate pushing arm 103 which engages a plate after it has been replaced into a lid-on at station C. The plate with lid on is then pushed to one of classification stacks D, E, F, or G along guide surface 104 of member 66.

In operation of the structure thus far described, magazine 13 is rotated to present a selected stack 14 of plates to the first transfer station. Then motor 54 drives pusher 51 to transfer a plate to lid-off station A. Cylinder 57 is operated to lift the lid, and cylinder 57 is then moved by motor 63 to carry the lid to lid-on station C. Transfer member 86 operated by motor 105 through gear box 106 indexes the plate to streaking station B and a streaking operation is performed. Then transfer member 86 is indexed to move the plate to station C. Cylinder 68 is operated to lift the plate into its lid, the motor 101 is operated to push the plate to a classification stack. It will be understood that transfer member 86 may be handling three plates simultaneously.

The streaking mechanism 110 is carried on an overhead support member 111 (FIG. 4) which is pivotally mounted to overhead frame 112 by means of links 113. A motor drive 114 rotates a crank 115 to move support member 111 as shown in FIG. 4. In the position shown in full line the streaking mechanism is picking up a liquid specimen from a specimen cup in specimen ring 31. At 111a the support is shown in the streak ready position, and at 111b it is shown in the streaking position. The specimen is carried in a flexible soft tube. As support 111 is pivoted to position 111b the edge of the tube is lightly laid on the surface of the agar, thus avoiding any digging action.

The motion of support 111 from the full line position of FIG. 4 is initially almost vertical as crank 115 moves upwardly. Then as crank 115 reaches a vertical position support 111 pivots to position 111a and then comes back to streaking position 111b to lay the end of the tube on the media.

Figures 5, 6:
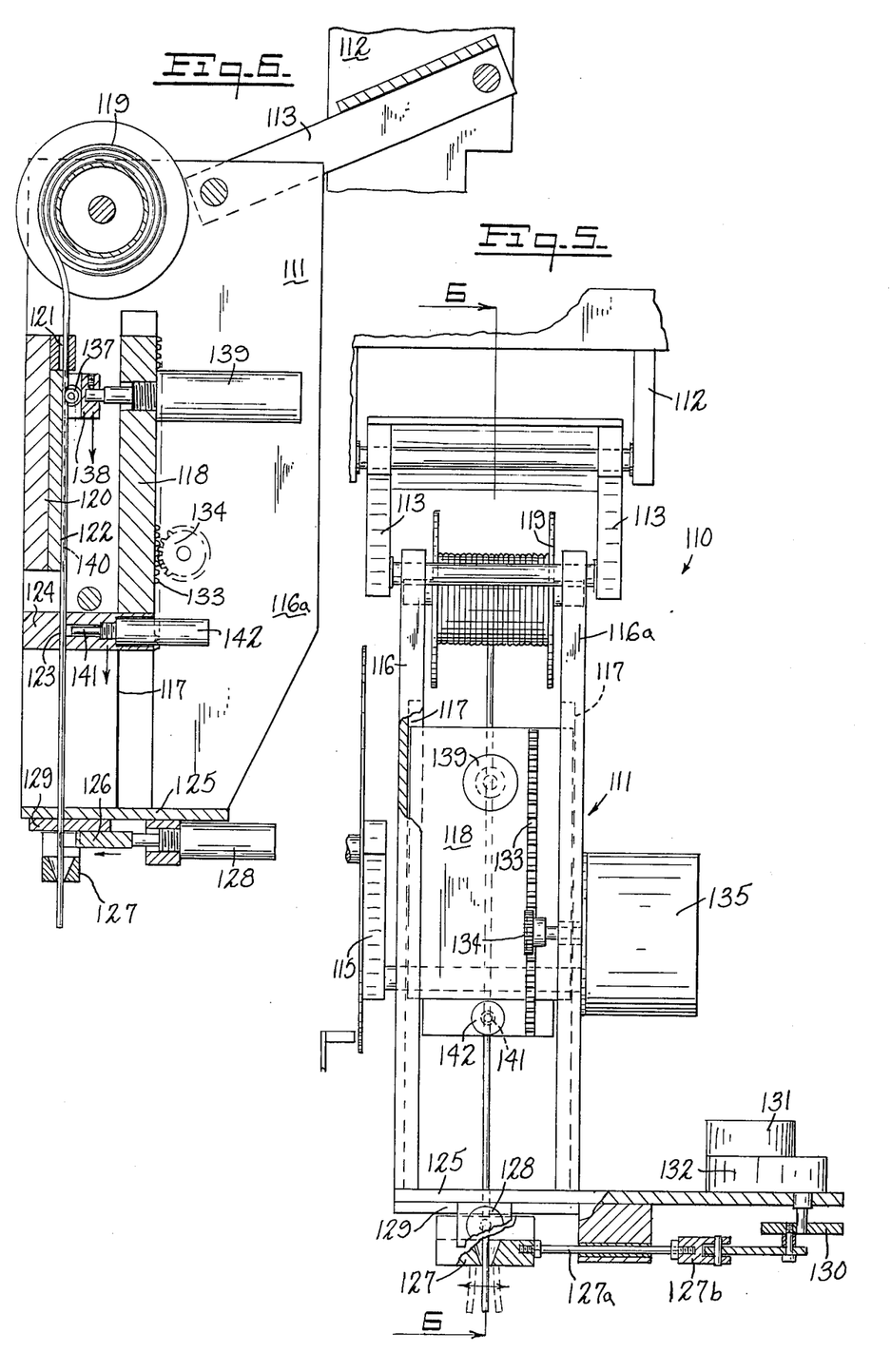
FIG. 5 is a front elevation of streaking apparatus embodying the invention.
FIG. 6 is a view seen in the plane of lines 6—6 of FIG. 5.
Figure 7:
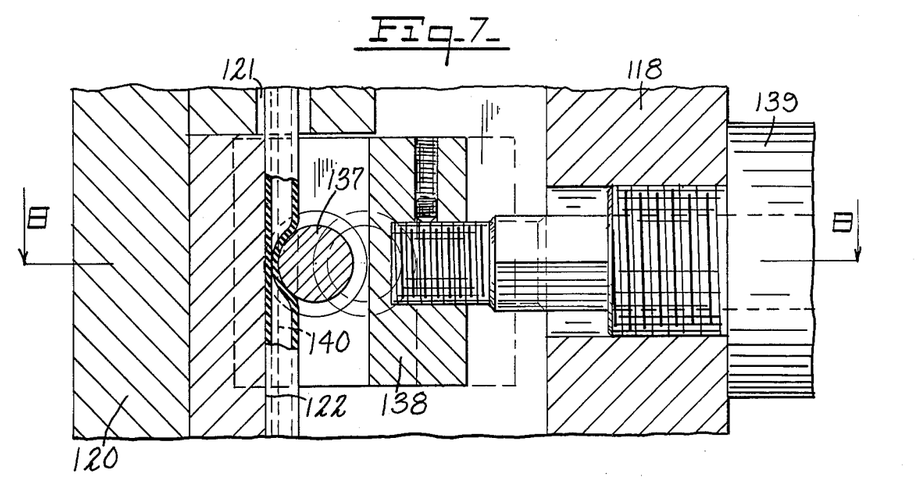
FIG. 7 is an enlarged view of a portion of FIG. 6.
Figure 8:
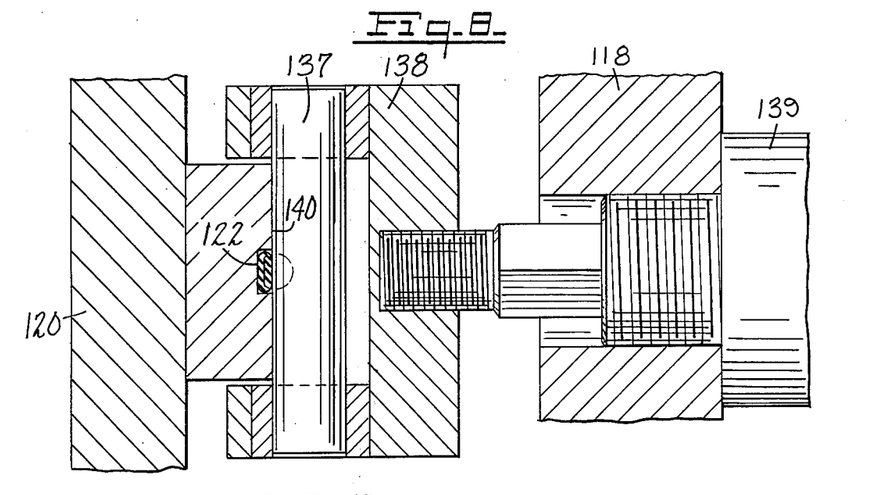
FIG. 8 is a view seen in the plane of lines 8—8 of FIG. 7.

Support member 111 (FIGS. 5 and 6) comprises spaced apart wall members 116 and 116a which define guides 117 for a member 118. A reel 119 for tubing is replaceably mounted between wall members 116 and 116a. A tubing guide member 120 extends between the wall members. Tubing from roll 119 extends through a passage 121 and then in a channel 122 (FIGS. 7 and 8) through a passage 123 in an extrusion 124 of 118, through base 125 past severing knive 126 and through an oscillatable guide member 127. Knife 126 is operated by a cylinder 128 and cooperates with a shear plate 129 to sever a used length of tubing. Oscillating guide member 127 is connected by a rod 128 and pivotal coupling 129 to a crank 130 driven by a motor 131 through a gear box 132.

Member 118 has a rack 133 thereon engaged by a pinion 134 on a stepping motor 135. Motor 135 is carried on wall 116. As more clearly shown in FIGS. 7 and 8, the tube resides in channel 121 which in depth, is very close to twice the wall thickness of the tube. A roller 137 is carried on a mount 138 which is movable by a cylinder 139 into and out of contact with surface 140a. Roller 137 may contact and collapse the tube without calendering it. A clamp 141 operated by solenoid 142 may engage the tube in passage 120 for purposes hereinafter described.

After a used length of tubing has been severed, the tube is clamped in passage 123, then motor 135 is operated to move member 118 downwardly and present a fresh length of tubing beneath guide 127. At this time the tip of the tubing is inserted into a specimen cup in ring 31. The clamp is released as roller 137 is moved to collapse the tubing. Motor 135 is operated to move member 118 upwardly a predetermined distance. This produces vacuum in the tube and an amount of specimen proportional to the travel of the roller on the tubing is aspirated into the tube.

Figure 10:
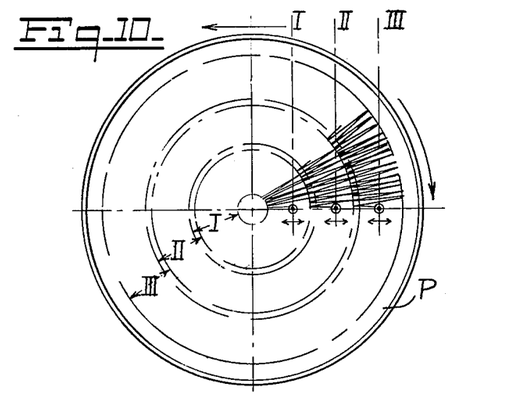
FIG. 10 exemplifies a streaking pattern on agar in a plate.

The support is then moved as previously explained to streaking position 111b. The tip of the tubing is initially at position I, FIG. 10, eccentric to the center of the plate. At this time, table 95 is rotated, while guide 127 is oscillated. This produces the first streaking pattern. During this streaking step the specimen is released at a controlled rate determined by the rate of downward movement of roller 137. Table 95 is then translated by cylinder 92 (FIG. 3) until the end of the tubing is at Position II (FIG. 10), then guide 127 again oscillates the end of the tube while table 95 is rotated. The extent of the oscillations is of greater magnitude than the translation of table 95 as shown in FIG. 10; therefore there is overlap of the extent of the oscillation between the streaking steps. After the second streaking step, table 95 is again translated by cylinder 93 so that the end of the tubing is a Position II and the third operation begins.

At the end of this streaking operation motor 114 moves support 111 back to streak ready position 111a to await the presentation of the next plate at position B if the next plate is to be streaked with the same specimen. At the conclusion of streaking all plates with the given specimen, support 111 is moved to a tube severing position, and cylinder 128 is operated to sever the length of tubing over a receptacle for such severed tubing. Then ring 31 is indexed to present the next specimen, support 111 is moved to the position shown in full line in FIG. 4. A new length of tubing is drawn down into a new specimen.

The disclosed embodiment of the invention utilizes the specimen in liquid form, however it will be understood that a microbiological specimen in any form such as soft solid, gel, mold may be applied to the end of a flexible tube and streaked by rotating the plate and translating either the plate or the center position of the tubing.

Various adjustments and variations in the method of streaking may be made. The streaking sections may be made to overlap or not overlap by adjusting the dimension plate 90 is translated by cylinders 92 and 93 and/or the amplitude of oscillations of guide 27 by varying the crank arm plate 130.

When a plate is streaked for colony count a precise amount of sample is evenly dispensed over the entire plate. When a plate is streaked for isolation the specimen is ejected only in Section I, and then streaked in diminishing dilutions in Section II and III. The overlap between Sections I and II draws some of the specimen into Section II. Likewise, the overlap between Section II and III draws some of the specimen into Section III during successive streaking steps.

Figure 11:
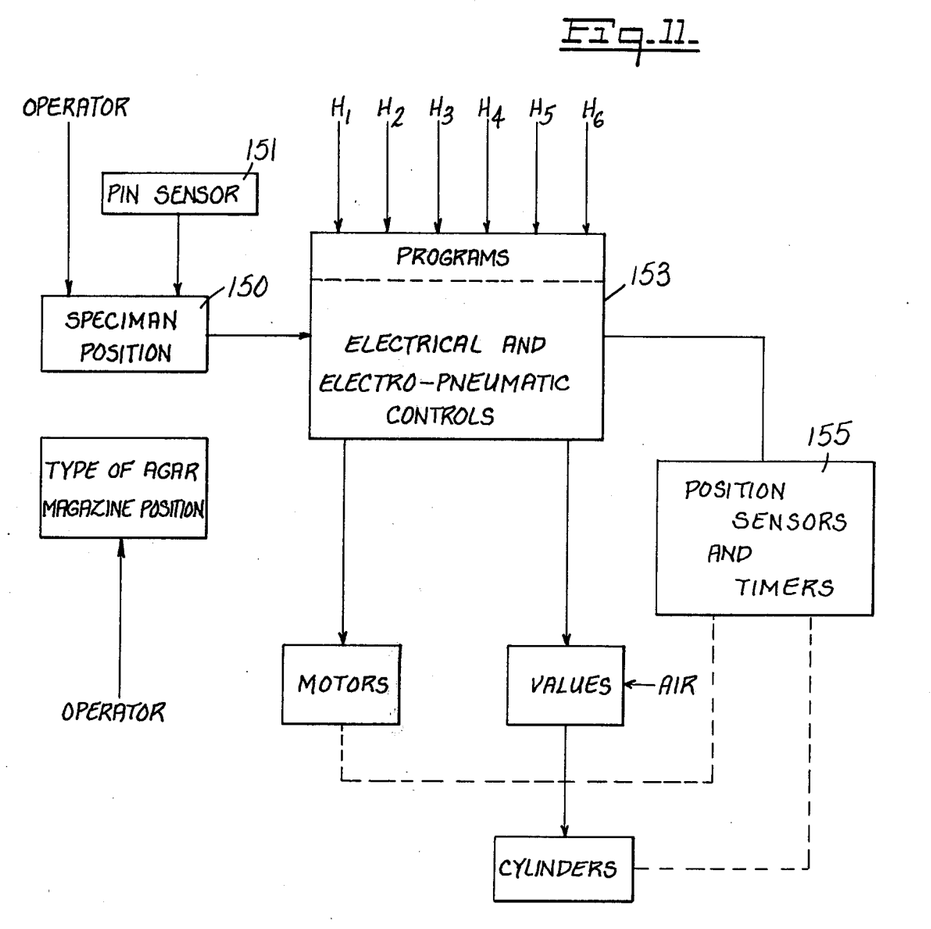
FIG. 11 is a block diagram of of a program and controls for operating apparatus embodying the invention.

Apparatus embodying the invention may be operated upon command by an operator, semi-automatically, or automatically under a program. Adjacent each cup recepticle 33 in ring 31 are apertures H to select up to six programs. A program of operation for a given specimen is selected by placing a magnetic contact pin in one of the holes H for a given specimen. This will set up a program $H_1$, $H_2$, $H_3$, $H_4$, $H_5$ or $H_6$ for that specimen. The programs are various combinations of types of agar plates, and streaking techniques. For example, programs $H_1$, may be to check for isolation on four different types of agar. The operator may optionally index ring 31 to the aspirating position shown in FIG. 4 by a control 150 or let the table index until a sensor 15 (FIG. 11) at that position senses the pin and stops the ring. The operator may also select the type of agar by rotating magazine 13 to the proper position by the selector 152, if the type of agar is not contained in the program. The program then takes over the electrical and pneumatic controls 153 for various cycles of operation. The controls are sequenced by sensing movements and positions of the various mechanisms and timing cycles for various operations as indicated by 154.

The overall operation is now summarized.

Upon receipt of a specimen, the operator places it in a cup and the cup into the sample ring 31. A program pin is inserted into one of program holes H adjacent the cup.

Member 30 is rotated by motor 37 until the program pin is detected by a light activated switch, and member 30 is stopped with the sample cup under the streaking mechanism in the sample pick-up position. Motor 21 is then energized to rotate magazine 13 until a selected column of plates is positioned in an un-load position under member 50.

When proper column of plates is positioned slide motor 54 runs pusher 51 in reverse to its rear limit clear of the selected column of plates and allows the column spring 15 to move the whole stack up one plate into the area vacated by the unload slide. On its forward travel pusher 51a transfers the top plate out to the lid-off Position A. The plate in the lid-off position is detected by a limit switch which energizes motor 63 to move slide 61 and cylinder 57 to Position A. Cylinder 57 moves cup 58 down onto the lid, and when piston 56 is extended solenoid valve is energized to apply vacuum to cup 58 and the plate lid is then removed and held up by lid-off cylinder 57. A limit switch responsive to retraction of the piston 56 of cylinder 57 causes the transfer member 86 to index the plate to position B. This occurs only after a timing cycle of sufficient length to permit the previous plate to be streaked, usually about fifteen seconds. This closes a limit switch which enables the streaking operation by mechanism 110.

Concurrent with this last sequence as soon as the sample cup is stopped in position B the streaker assembly is indexed through motor 114 from the streak-ready position 111a to a tube cut-off position (not shown) where cylinder 128 drives knife 126 across shear plate 127 to shear the previous length of sample tube over a tube cut-off collection recepticle.

The roller pump cylinder 139 is de-energized and the stepper motor drives the tube carriage to a predetermined position upwardly. Cylinder 142 then moves clamp 141 into engagement with the tube. Stepper motor 135 drives member 118 down to its lower limit. Since the tube is now clamped to member 116 it is pulled down from the pay-off reel 119 and fed down through base 122 and oscillator guide 127.

Simultaneously, the streaker support 111 was moved by motor 114 from the tube cut-off position to the sample pick-position as shown in FIG. 4. The new tube that is being run out is actually fed into the sample cup in this position. When the stepper motor 135 reaches its bottom limit, the tube clamp air cylinder 142 is deenergized, unclamping the tube from the carriage. The roller pump air cylinder 139 is energized and closes the roller on platen surface 140a with the tubing in channel 122. The stepper motor 135 now moves member 118 to a sample pick-up position which is predetermined. As the roller moves up the pinch point caused by the roller on the platen also moves up, aspirating the specimen into the tube.

After the specimen is picked up, motor 114 moves the streaker assembly to the streak-ready position to await a streak enable signal, which indicates that a new plate is in the streaking position. This signal is provided by a sensor, either optical or mechanical. When this signal occurs, the structure 111 is driven by motor 114 so that as the tubing is brought down to the agar surface it is laid on in an arc with the tube opening on the trailing side. At this time the tube is being oscillated and the plate is being rotated. These three factors prevent the tubing from digging into the soft agar or die cutting a plug to close the end of the tube.

The tubing is brought into contact with the plate eccentric to the center shown as Position I, FIG. 10. The combined action of the swinging tube and the turning plate covers Section I (FIG. 10) of the plate with the end of the tube. The stepper motor concurrently steps down the amount predetermined for count or for isolation as determined by a program thereby expelling the precise amount of sample on the plate in Section I, in an annulus.

After a preset adjustable time, plate 90 with the agar plate thereon, is translated by cylinder 92 so that the oscillating tube now describes second annulus shown as Section II around Secion I. The amplitude of oscillation over Section II, as shown, is such that it slightly overlaps Section I. After another preset but adjustable time, plate 90 is translated again by cylinder 93 so that the swinging tube now describes a third annulus shown in Section III, overlapping a portion of Section II.

At the completion of the streaking of Section III the plate is allowed to stop and an antibiotic disk may be dropped if desired. This is optional. The streaker assembly then indexes back up to the streak-ready position 111a for the next plate. Concurrently with the streaking action the lid held up by cylinder 66 and cup 58 is translated to Position C. Air cylinder 57 is energized, lowering the lid into the lid-on well on retainers 71a and the vacuum is broken. Cylinder 56 is now returned on guide 61 to the Position A to act on the next plate.

Air cylinder 68 moves the streaked plate up through the lid in position C, thereby replacing the lid. Slide 100 moves the plate to the selected incubator stack D, E, F, or G that has been determined, and air cylinder 74 moves the plate up into one of the stacks.

The described cycle of operation is accomplished with a sequencing control which includes sensors in the form of limit switches, or light responsive switches. For example, the position of the streaker is sensed by non-reflective portions on an encoder disk 150 (FIG. 5) and a light sensitive switch 151.

Depending on the program, another plate may be fed from the same stack for a different type of streaking, or the magazine 113 may have been rotated during the previous streaking operation or previous delivery to Position A to present a different type of agar plate.

It may thus be seen that the objects of the invention set forth as well as those made apparent from the foregoing description are efficiently attained. While preferred embodiments of the invention have been set forth for purposes of disclosure, modification to the disclosed embodiments of the invention as well as other embodiment thereof may occur to those skilled in the art. Accordingly, the appended claims are intended to cover all embodiments of the invention and modifications to the disclosed embodiments which do not depart from the spirit and scope of the invention.

What is claimed is:

1. Apparatus for streaking media with a specimen comprising a magazine for selectively storing plates containing various agar media having lids thereon and movable to present a selected plate to a delivery position, means for delivering a selected plate to a first position, means for removing the lid at said first position, means for streaking a specimen on the media in said plate, means for moving said plate after streaking to another position and replacing the lid thereon, and means for moving said plate from said lid replacing position to a pick-up position, said means for delivering comprising a pushing mechanism arranged to push a plate from a selected stack in said magazine from said delivery position to said first position, and further means for transferring the plate to a second position for streaking prior to transfer to said another position.

2. The apparatus of claim 1 wherein said magazine is refrigerated.

3. The apparatus of claim 1 wherein the plates are classified as to media and stored in vertical stacks in accordance with the classifications in a movable magazine.

4. The apparatus of claim 1 wherein said magazine comprises vertical guide means for stacks of plates, and means in each guide means for biasing a stack of plates upwardly.

5. The apparatus of claim 1 wherein said means for removing the lid comprises a suction operated device movable on a cylinder, and means for moving said cylinder from said first position to said another position.

6. The apparatus of claim 5 wherein the lid is replaced at said another position by lifting a plate into the lid.

7. The apparatus of claim 1 further including a holder for the lid at said another position.

8. The apparatus of claim 7 wherein a pivotal loading guide is provided with a passage therethrough and said holder is in said passage, said means for lifting lifts the plate through said passage into said lid, and means on said pivotal guide for transferring the plate with lid thereon to the pick-up position.

9. The apparatus of claim 1 further comprising a rotatable support member for a plate in said second position, and means for rotating said support member with a plate thereon while simultaneously introducing a specimen in oscillating motion radially of the media eccentric to the center of the media.

10. Apparatus for streaking agar in a plate with a liquid sample comprising a support member, rotatable means for supporting a plate, a guide on said support member for a length of flexible tubing, a member on said support member movable along said guide means, means providing a supply of flexible tubing to said guide means along said support member, means for moving said support member to position the end of the tubing in a sample, and to position the end of the tubing on the agar in a plate on said rotatable means, contact means on said movable member for engaging the tubing in said guide means and progressively collapsing said tubing whereby said tubing aspirates the sample as said contact means moves upwardly on the tubing, and dispenses the sample as the contact means moves downwardly on the tubing, and means for oscillating the end of the tubing in said guide means eccentric to the center of the plate while said rotating means rotates the plate as said contact means dispenses the sample from said tubing.

11. The apparatus of claim 10 further including means on said guide means for limiting movement of said contact means to collapse the tubing.

12. The apparatus of claim 10 wherein said tube guide means includes a channel for receiving a length of tubing therein, said channel having a depth approximately twice the dimension of the wall thickness of the tubing.

13. The apparatus of claim 12 wherein said channel is recessed behind a surface and said surface determines the position of said contact means in collapsing the tubing.

14. The apparatus of claim 10 further including means for severing a length of tubing after use thereof for streaking.

15. The apparatus of claim 10 further including tube clamping means on said movable member whereby tubing may be clamped in said movable member and drawn from said supply when said movable member moves downwardly.

16. The apparatus of claim 15 further including the severing means on said support member between said clamping means and said means for oscillating.

17. The apparatus of claim 10 further including a first pivotal crank connected between said support member and a support structure, drive means, a drive crank of shorter length connected to said drive means and pivotally connected to said support means whereby said drive crank is driven by said motor, said support member is first moved substantially vertically from a sample aspirating position and then moves pivotally to a sample ejecting position such that the tube end approaches the plate in an arc with the tube opening on the trailing side.

18. The apparatus of claim 10 further including means for moving said support member to a sample ejecting position such that the tube end approaches the plate in an arc with the tube opening on the trailing side.

19. A streaking apparatus in which a specimen is aspirated into a flexible tube and dispensed therefrom onto a media, comprising means for providing a supply of tubing, means defining a guide for the tubing, means for engaging the tubing and pulling it from the supply along said guide, a member having a tubing contacting means movable along said guide, means for moving said contacting means to cause said contacting means to contact and at least partially collapse the tubing so that when said contacting means is moved in a first direction on the tubing a specimen may be aspirated into the tubing and when said engaging member is moved in the other direction on the tubing the specimen may be dispensed from the tubing.

20. The apparatus of claim 19 wherein said means for pulling comprises a releasable clamp on said member for engaging tubing in said guide.

21. The apparatus of claim 19 comprising means for severing tubing extending through said guide.

22. The apparatus of claim 19 wherein said means providing a supply is a reel mounted above said guide.

23. The apparatus of claim 19 further including means for limiting compression of said engaging means on the tubing.

24. A method of streaking an agar sample with a specimen in an open dish comprising the steps of placing the specimen in a specimen carrier, contacting the end of the carrier to the agar sample eccentric to the center of the dish, oscillating the end of the carrier and simultaneously rotating the dish and dispensing the specimen from the carrier onto the sample to provide an annulus of the specimen on the sample.

25. The method of claim 24 comprising the further steps of linearly translating the dish, again oscillating the end of the carrier in contact with the agar while rotating the dish.

26. The method of claim 25 where the carrier is a hollow tube and the extent of movement of the end of the tube on the agar during said second oscillation partially overlaps the extent of movement of said carrier during the first oscillation.

27. The method of claim 26 wherein no specimen is dispensed from the tube during said second oscillation.

28. The method of claim 24 where the carrier is a hollow tube, the specimen is liquid and the specimen is introduced into said tube, by inserting the end of the tube into the specimen, and thereafter collapsing said tube progressively with a roller in a direction away from said tube end to create a partial vacuum in said tube.

29. The method of claim 24 where the carrier is a hollow flexible tube and the specimen is released from said tube by collapsing said tube with a roller moved toward the end of said tube.

30. The method of claim 24 where the carrier is a hollow flexible tube and the end of the tube is moved in an arc into contact with the agar with the end of the tube trailing.

31. Apparatus for streaking media with a specimen comprising a rotatable support member for a media containing plate, a member disposed above said support member and carrying a length of flexible tubing thereon, means for filling said tubing with a streaking specimen and dispensing the specimen therefrom, means for moving said member so that the end of said tubing contacts media in a plate on said support member eccentric to the center thereof, means for rotating said support member, and means for oscillating the end of said tubing while dispensing liquid from the tubing to define an annulus of the specimen on the media.

32. The apparatus of claim 31 further including means for translating said rotatable support member with respect to said member.

33. The apparatus of claim 31 further including a supply of said tubing, a guide for said tubing on said member, means on said member for engaging said tubing and at least partially collapsing said tubing and then moving along a length of said tubing whereby when said engaging means moves upwardly on said tubing a partial vacuum is formed therein and specimen may be aspirated into said tubing, and when said engaging means moves downwardly on said tubing the aspirated specimen is dispensed therefrom.

34. Apparatus for aspirating and dispensing a liquid specimen comprising, a support member, a guide on said support member for a length of resilient tubing, means for providing a supply of resilient tubing to said guide means, a member mounted on said support member and movable along said guide means, said member carrying an engaging member arranged to move into and out of contact with tubing in said guide means and at least partially collapse tubing in said guide means when in contact therewith, means for moving said member, and means for moving said engaging member, whereby when said member is moved along said guide means in an upwardly direction with said engaging means in contact with said tubing, a liquid specimen may be aspirated into said tubing and when said engaging means is moved downwardly in contact with said tubing a liquid specimen therein may be dispensed therefrom.

35. The apparatus of claim 34 further including a tube grasping means on said member arranged to grasp tubing extending from said guide means, whereby when said member moves downwardly on said support member with said grasping means engaging the tubing a new length of tubing is pulled from said supply means.

36. The apparatus of claim 35 further including tube severing means mounted to said support means for severing a used length of tubing from the end of the length of tubing.

37. The apparatus of claim 34 further including an oscillatable guide member carried on said support member and arranged to receive an end of the tubing therethrough, and means for oscillating said oscillatable member.

38. The apparatus of claim 34 further including means for pivotally moving said support member between a position where the end of tubing on said support member is positioned in a specimen for aspirating the specimen and a position where said specimen is to be dispensed.

39. Apparatus for aspirating and dispensing a fluid comprising means providing a guide for a length of resilient tubing, a member movable along the length of said guide means, a tube engaging means on said member mounted for movement toward and away from said guide, means for moving said engaging means toward said guide to at least partially collapse tubing thereon, means for moving said engaging means along said guide in a position to collapse the tubing, another member having an opening therethrough for receiving an end of the tubing and means for oscillating said second member in a direction substantially perpendicular to said guide means.

40. Apparatus for streaking media with a specimen, comprising a platform for a media container, means for rotating said platform, means for translating said platform, a specimen dispensing apparatus comprising a support member, a guide for flexible tubing on said support member, a tubing engaging member adapted to contact the tubing and at least partially collapse the tubing, means for moving said engaging member along the length of the tubing to aspirate a specimen into said tubing and to dispense the specimen therefrom, and means for moving said support member between a position to aspirate a specimen into the tubing and a position to dispense the specimen in a media container on said platform.

* * * * *